(12) United States Patent
Simond et al.

(10) Patent No.: US 7,075,537 B2
(45) Date of Patent: Jul. 11, 2006

(54) APPARATUS FOR MEASURING A BIOLOGICAL PARAMETER EQUIPPED WITH A GRAPHIC REPRESENTATION DISPLAY

(75) Inventors: Bénédicte Simond, Bloye (FR); Yves Patras, Poisy (FR)

(73) Assignee: SEB S.A., Ecully (FR)

( * ) Notice: Subject to any disclaimer, the term of this patent is extended or adjusted under 35 U.S.C. 154(b) by 86 days.

(21) Appl. No.: 10/497,298

(22) PCT Filed: Nov. 27, 2002

(86) PCT No.: PCT/FR02/04054

§ 371 (c)(1),
(2), (4) Date: Jun. 1, 2004

(87) PCT Pub. No.: WO03/046493

PCT Pub. Date: Jun. 5, 2003

(65) Prior Publication Data

US 2004/0262046 A1 Dec. 30, 2004

(30) Foreign Application Priority Data

Nov. 30, 2001 (FR) .................................. 01 15493

(51) Int. Cl.
- *G09G 5/22* (2006.01)
- *A61B 5/05* (2006.01)
- *G01G 23/36* (2006.01)
- *G01G 19/414* (2006.01)
- *G01G 19/50* (2006.01)

(52) U.S. Cl. .................... 345/440.2; 345/35; 345/55; 177/25.16; 177/25.19; 177/177; 600/484; 600/547

(58) Field of Classification Search .............. 345/33, 345/35, 55, 440.2; 177/177, 25.16, 25.19; 600/484, 547
See application file for complete search history.

(56) References Cited

U.S. PATENT DOCUMENTS

| | | | | |
|---|---|---|---|---|
| 3,531,795 | A | * | 9/1970 | Gassler ........................ 345/24 |
| 4,113,039 | A | | 9/1978 | Ozaki et al. ............. 177/25.19 |
| 4,447,884 | A | * | 5/1984 | Wada ......................... 702/131 |
| 4,629,015 | A | * | 12/1986 | Fried et al. ............. 177/25.19 |
| 4,689,615 | A | * | 8/1987 | Del Rosso ............... 345/440.2 |
| 5,705,747 | A | * | 1/1998 | Bailey ...................... 73/290 R |
| 5,788,655 | A | * | 8/1998 | Yoshimura et al. ......... 600/587 |
| 5,817,031 | A | * | 10/1998 | Masuo et al. ............... 600/547 |
| 6,308,096 | B1 | * | 10/2001 | Masuo ....................... 600/547 |
| 6,354,996 | B1 | * | 3/2002 | Drinan et al. .............. 600/300 |
| 6,516,221 | B1 | * | 2/2003 | Hirouchi et al. ........... 600/547 |
| 6,516,222 | B1 | * | 2/2003 | Fukuda ...................... 600/547 |
| 6,665,561 | B1 | * | 12/2003 | Baba et al. ................. 600/547 |
| 6,704,012 | B1 | * | 3/2004 | Lefave ....................... 345/440 |
| 6,956,572 | B1 | * | 10/2005 | Zaleski .................... 345/440.2 |

FOREIGN PATENT DOCUMENTS

EP  1 120 083 A2  1/2001

(Continued)

*Primary Examiner*—Randy W. Gibson
(74) *Attorney, Agent, or Firm*—Browdy and Neimark, PLLC

(57) ABSTRACT

The invention concerns an apparatus for measuring a biological parameter of an individual comprising measuring means, means for storing and/or for computing values of said parameter connected to a display (3) for graphic representation of the measured parameter relative to a representation axis. The invention is characterized in that said display (3) is designed to adjust the measured parameter relative to a reference zone delimited on either side on said axis by a fixed mark combined with at least an adjacent digital indication.

18 Claims, 4 Drawing Sheets

FOREIGN PATENT DOCUMENTS

| | | | |
|---|---|---|---|
| EP | 1 095 613 A1 | 5/2001 | |
| JP | 55124009 A * | 9/1980 | ................ 345/35 |
| WO | WO 99/52425 | 10/1999 | |
| WO | WO 00/58697 | 10/2000 | |
| WO | WO 03/046493 A1 | 6/2003 | |

* cited by examiner

APPARATUS FOR MEASURING A BIOLOGICAL PARAMETER EQUIPPED WITH A GRAPHIC REPRESENTATION DISPLAY

The present invention concerns an apparatus for measuring a biological parameter, such as weight, body composition, size, temperature, blood pressure, cardiac rhythm, etc., of an individual and it concerns more particularly a device for graphic representation of said parameter.

So-called "digital" measurement apparatus for biological data of an individual have, generally, measuring means connected to means for storing and/or computing the value of said parameter, these latters being connected to means for displaying the measured or computed value on the basis of measurements effectuated by the apparatus. This means for displaying are presently constituted by a liquid crystal display adapted to indicate the measured value of said parameter by an alphanumeric representation or by a graphic representation, in the form of juxtaposition of points, a curve, or a histogram, or even by a combination of these two types of representation.

The measured values of a biological parameter are different from one individual to another and they vary with time for the same individual. It is thus preferable that such an apparatus can compare the current measured value with another previously stored or predetermined value in the memory of the apparatus and then display a comparison between two or several values or a tendency of evolution of the values of the measured biological parameters.

The document U.S. Pat. No. 4,113,039 describes an apparatus for measuring the body weight of an individual, this apparatus being furnished with a digital display of the measured weight and of its relation with respect to a standard weight. The standard weight is evaluated by the apparatus for each individual as a function of his height, his age, his gender and his nationality. Then, the display indicates in digital form the measured weight and the difference with respect to the standard weight, a signal light being also actuated to indicate if the weight is normal, below or above the computed standard value. Such a digital display has the drawback, on the one hand, of requiring a screen of rather large dimensions to make the two groups of numbers readable which causes the size of the apparatus to be increased and, on the other hand, of presenting a uniquely digital message, thus not well understandable.

In the document WO 99/52425 is described an apparatus for measurement of the body weight of a person, this apparatus having a combined digital and graphic display of the measured data and of their evolutions with time. The display has a first digital display zone for the present values of the weight and the fat content of the body of the person and a second graphical representation zone using point matrices, of the two parameters and their evolution with time. Such a display requires a large number of points, which causes the display to be complex and costly.

An apparatus of the same type having a combined digital and graphic display has been described in the document EP 1 120 083. The graphic representation zone is produced in the form of a matrix of elongated rectangular segments having time on the abscissa and the value of the measured parameter on the ordinate. This display permits indication of the current value of a parameter and representation of its evolution with time, the representation being able to be made in three graduation values in order to take into account the differences due to the fluctuation over time of the measured values of said parameter. This display shows the evolution of the body composition of a person in a simplified manner with respect to the preceding, but it has been found however to be of a limiting use, since it must effectuate a substantial number of readings in order to render the interpretation understandable. Moreover, with such an apparatus, the user can measure the current value of a parameter and compare it with previous values, without knowing if the measured value or its evolution are within the normal limits adapted to the person who uses the apparatus.

Moreover, Dr. Boulier—Paris University V—Paris—France originated a program implemented on a multi-media platform permitting to be displayed on the screen of a computer, connected to an apparatus for measuring a biological parameter, a simultaneous graphic representation of the values of several biological parameters measured by the apparatus. The representation of the parameters is given with respect to theoretical limits, lower and upper, pre-established for each parameter. Display of the value of each parameter is achieved in the form of a point on a line comprising a practically infinite number of points. The lower and upper limits of all of the measured parameters being fixed, the representation of each parameter with respect to each of its respective limits is provided by an adjustment of the scale of the representation of its axis. This program already permits a simplified graphic representation of several biological parameters simultaneously, but it has its limits during interpretation by the user of the screen image. Thus, it has been found that the user has difficulty in deciphering the message on the screen since he only see points on lines, without precise understanding of the value of the points that he observes. Moreover, such a reading requires a great deal of concentration, which, eventually, could prove tiring for the user. In addition, this program requires a high-performance multi-media platform distinct from a bathroom scale or from a simple apparatus for biological parameter measurement.

The goal of the present invention is to overcome the above-cited drawbacks and to provide an apparatus for measuring a biological parameter of an individual having a display permitting a precise graphic representation while being simplified, adapted to facilitate interpretation by the user of the measurements made.

Another goal is an apparatus for measuring a biological parameter of an individual having a display for graphic representation of the measured values permitting their comparison with normal values adapted to the individual.

Another goal of the invention is an apparatus for measuring a biological parameter of an individual, having a graphic representation display of simplified construction and able to be mass produced at a reduced cost.

These goals are achieved with an apparatus for measuring a biological parameter of an individual having measuring means, means for storing and/or computing values of said parameter connected to a display for graphic representation of the measured parameter relative to a representation axis, by the fact that said display is adapted to adjust the position of said measured parameter with respect to a reference zone delimited to one side and the other of said axis by a fixed mark in combination with at least one adjacent digital indication.

The reference zone of a biological parameter associated with an individual is understood to be a range of values demarcated by values evaluated by the apparatus or selected by the individual as a function of the different data specific to this latter. Thus, these values forming a reference zone can be target values selected by the individual to improve his performance or they can be represented by normality values of a parameter. These normality values can be evaluated by a computing unit of the apparatus as a function of different conditional date such as height, age, gender, physical condition, etc.

A fixed mark of a representation axis is understood to be a point situated on an axis constituted by a plurality of points, a mark that is always represented in the same position when the display is placed in operation. Moreover, one can equally understand that said mark is applied or engraved on an upper part of the display that is superimposed on that containing the representation axis and leaves said axis visible, in a manner such that said mark merges with one of the points on said axis.

According to the invention, said display is able to adjust the position of the measured parameter with respect to the two marks fixed on the representation axis in a manner such that the measured valued can be represented on said axis with respect to a reference zone. Thus, the measured value can be disposed to one side or the other of the reference zone, i.e. outside of the fixed marks or between the two marks, as a function of the difference between the measured value of the parameter and that corresponding to the closest mark. Such a representation causes the significance of the digital value displayed to the side to be understandable, while relying on much simpler representation means, particularly a point on an axis with respect to a reference zone.

Consequently, this graphic representation already permits the position of each value to be visually situated with respect to its reference zone and thus facilitates interpretation.

Moreover, by attributing specific values to the fixed marks, one arrives at representing on the same axis values of the same parameter for several different individuals since the fixed marks are always represented in the same reference zone, and only their affected values vary according to the individual.

Moreover, the display according to the invention has at least one digital indication adjacent to the graphic representation zone. This digital indication is thus located in a digital display zone of the measured and/or computed values of the biological parameter under consideration disposed in proximity to the graphic display zone in order to facilitate reading. This digital display zone permits the user to be informed of the exact value of the parameter measured and graphically represented and, moreover, to verify the correct capture of the data specific to each user. Thus, reading of the digital values combined with that of the graphic representation of the same values with respect to a pre-established reference zone permits a better visual location of the point on the graphic, with respect to its variation limits, while having available the digital signification of this point and/or that of its limits. This facilitates interpretation by the user of the values represented on the screen and permits the precision and speed of reading to be improved.

The apparatus of the invention thus comprises a simplified display, which can be integrated into the measuring apparatus or situated at a distance with respect to this latter, while being connected to the apparatus by a cable or by a remote transmission means. This display has a simplified resolution, with respect to that of a computer screen which is nearly infinite. The display of the invention has an optimum number of segments calculated to permit, on the one hand, a good interpretation of the values of the measured parameter and, on the other hand, a reduced manufacturing cost.

Usefully, said computing means effectuate a calibration of the graphic representation scale as a function of the value attributed to the width of the zone comprised between the two fixed marks.

Adjustment of the position of the measured value is made by a calibration of the scale of representation by considering the value of a graduation, or value of a point on the axis equal to the difference between the values attributed to each of the marks divided by the number of graduations constituting, on the representation axis, the width of the zone delimited by the two fixed marks.

Advantageously, said fixed marks delimit, to one side and the other of the center of said axis, an interval of normality of the measured parameter.

Thus, the two fixed marks form upper and lower limits of variation of said parameter in a pre-established normality band for each individual. The normality band can be determined by standards established for each individual as a function of his personal data (age, gender, height, etc.) while taking into consideration the average and standard deviations calculated from measurement of said parameter performed on a statistically representative sample of each category of individual. The two fixed marks are advantageously positioned to one side and the other of the center of the axis in order to facilitate interpretation and to be able to inscribe the variations in the two directions, increasing or decreasing variation of the measured parameter.

Preferably, said display is adapted to graphically represent at least two distinct parameters simultaneously.

One can thus represent the position of several parameters of different orders of magnitude with respect to the same zone of normality, which permits a simultaneous interpretation of the value of certain parameters linked to one another or which make reference to the same state of the individual, for example the weight and the quantity of fat mass.

Advantageously, said display is adapted to display digital indications of one parameter at a time, and it comprises means for switching over to the display of digital indications of another parameter.

This permits simplifying the display which has by this fact a smaller number of segments. Moreover, the digital indication can occupy a larger zone of the screen of the display which permits the display of the digital indication in large dimensions, more visible to the user.

Preferably, said display is adapted to display intermittently the digital indications of each parameter and it has a cursor linking the graphic representation to the digital indication of said parameter.

This permits scrolling of the digital values on the screen, all while viewing their graphic representation which is permanent, in order to be able to compare the two measured parameters with one another. A cursor is advantageously situated adjacent the graphic representation axis of each parameter, the cursor becoming active at the moment when the digital display indicates the values of the graphically represented parameter in order to form the linkage between the graphic representation of a given parameter and its digital values displayed on the screen.

Advantageously, said at least two parameters are represented on parallel axes.

Each parameter is thus represented on a distinct axis, parallel to the axis of representation of the other parameter, which facilitates reading and comparison of the two parameters with respect to one another.

Preferably, said marks are constituted by two parallel lines that cross said axes and define a zone of normality for the measured parameters.

This permits the constitution of a single zone of normality, which has the same value for all of the measured parameters and which permits at the same time comparative analysis of the parameters that are normally expressed in different units of measurement.

Advantageously, said parallel lines are vertical, which implies an arrangement of the axes of representation in a horizontal position. This permits a large range of values to be represented on each axis, all while using a display of reduced dimensions.

In a preferred embodiment of the invention, said parameters are the weight, the quantity of fat mass, and the quantity of lean mass of the individual.

With apparatus according to the invention, one can display graphically and simultaneously several characteristics and parameters of a specific state of the individual, for example the state of health of a person is well illustrated by the weight, the quantity of fat mass, the BMI representing the ratio between the weight and the square of the height, the quantity of water in the tissues, etc. It is preferred however to compare the relation among three of these parameters, notable weight, quantity of fat mass and quantity of lean mass, since these are related parameters the comparison of which permits the user to establish his proper health assessment.

In another embodiment of the invention, said parameters are the height, the weight, and the body mass index.

The body mass index, also called BMI, permits a determination, in a simple and rather reliable manner, of an excess or insufficience of weight. The body mass index is calculated in relating the weight, in kilograms, to the square of the height, in meters. Thus, the display of the invention permits a simultaneous representation of these three linked parameters, representative of a weight state of an individual, with respect to a pre-established normality zone.

Preferably, the graphic representation axis of said display is constituted by a succession of 10 to 20 points.

It has been noted that on such an axis, one can represent a large range of parameters and their zone of normality, which permits use of a display having a limited number of points and thus simplification of the control circuit of the display and reduction of the cost thereof. Such a display can be integrated into an apparatus for measuring a biological parameter, without for that matter increasing in a significant manner the cost of the apparatus.

Preferably, the apparatus according to the invention is able to represent the biological parameters specific to several individuals.

Thus, the apparatus is provided with a memory having a sufficiently large capacity to store data relating to several users in order to recognize the user and store the measurements concerning him as they are collected.

Advantageously, the apparatus according to the invention has means for placing in memory measured values and for display of the history of the evolution over a predetermined period.

One can thus imagine a display having, for each parameter, a matrix of points with, for example, a time axis on the abscissa and an axis of measured values on the ordinate. This permits visualization of the evolution of each parameter over time and, at the same time, with respect to the zone of normality such as previously defined.

The characteristics of the invention can advantageously be found in an apparatus for measuring the body composition of an individual, having measuring means, means for storing and/or for computing the values of at least one parameter of the body composition, connected to a display for graphic representation of the measured parameter with respect to a representation axis, by the fact that said display is adapted to adjust the position of said measured parameter with respect to a reference zone delimited to one side and the other on said axis by a fixed mark, in combination with at least one adjacent digital indication.

The characteristics of the invention can equally be found in a bathroom scale or a child's scale having means for measuring a parameter, such as weight or height, means for storing the measured values and/or for computing, on the basis of values measured and/or inputted by means of a keyboard, values of at least one supplementary parameter, these means being connected to a display for graphic representation of the measured and/or computed parameters with respect to a representation axis, characterized in that said display is able to adjust the position of the measured and/or computed parameter with respect to a reference zone delimited to one side and the other on said axis by a fixed mark in combination with at least one adjacent digital indication.

The invention equally concerns a process for measuring biological parameters of an individual having steps of measuring the values of said parameters, of storing in memory the measured values and/or of computing values of said parameters, of graphic display of the measured parameter with respect to a representation axis, by the fact that it has a step of adjustment of the position of said measured parameter with respect to a reference zone delimited at one side and the other on said axis by a fixed mark, and of representation in combination with at least one adjacent digital indication.

Other characteristics and advantages of the invention will appear more clearly in light of the description and the drawings that follow illustrating, by way of non-limiting example, an embodiment of the invention. Thus, reference is made to FIG. 1 to 5, where:

Figure 1:
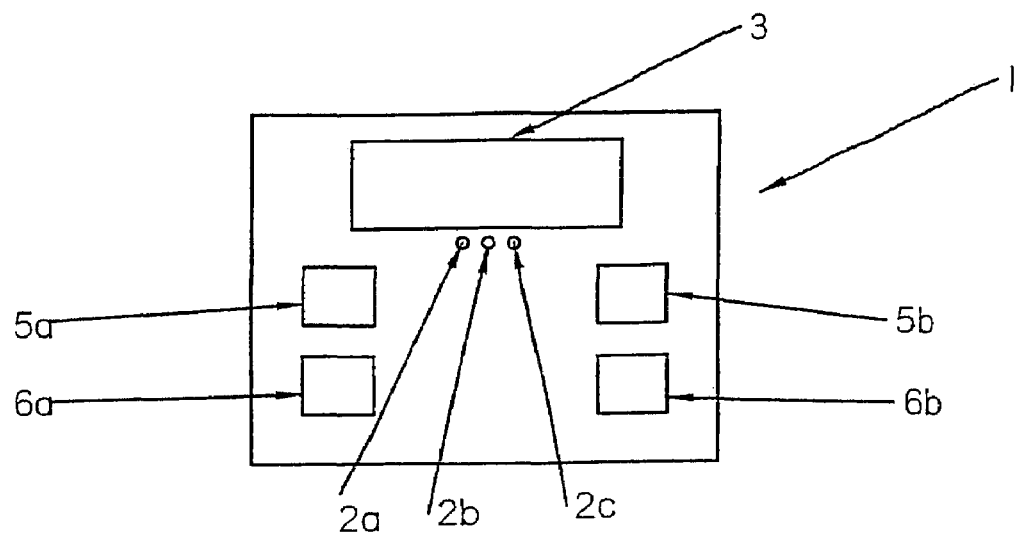
FIG. 1 shows a top view of an apparatus according to the invention.

In FIG. 1 is shown a measurement apparatus 1 for the body composition of an individual based on measurement of a bioelectric impedance. Such an apparatus utilizes the association of a bathroom scale platform and a plate furnished with four electrodes. Two of these electrodes, called excitation, 5a,5b are associated with a circuit for application of a signal between two points of the body of the individual, while the other two are measurement electrodes 6a, 6b. Measurement apparatus 1 has selection buttons 2a,2b,2c for values specific to the individual which are then displayed on the screen of display 3. Such a type of apparatus is described in greater detail in the document FR 01-13193 in the name of the applicant.

Figure 2:
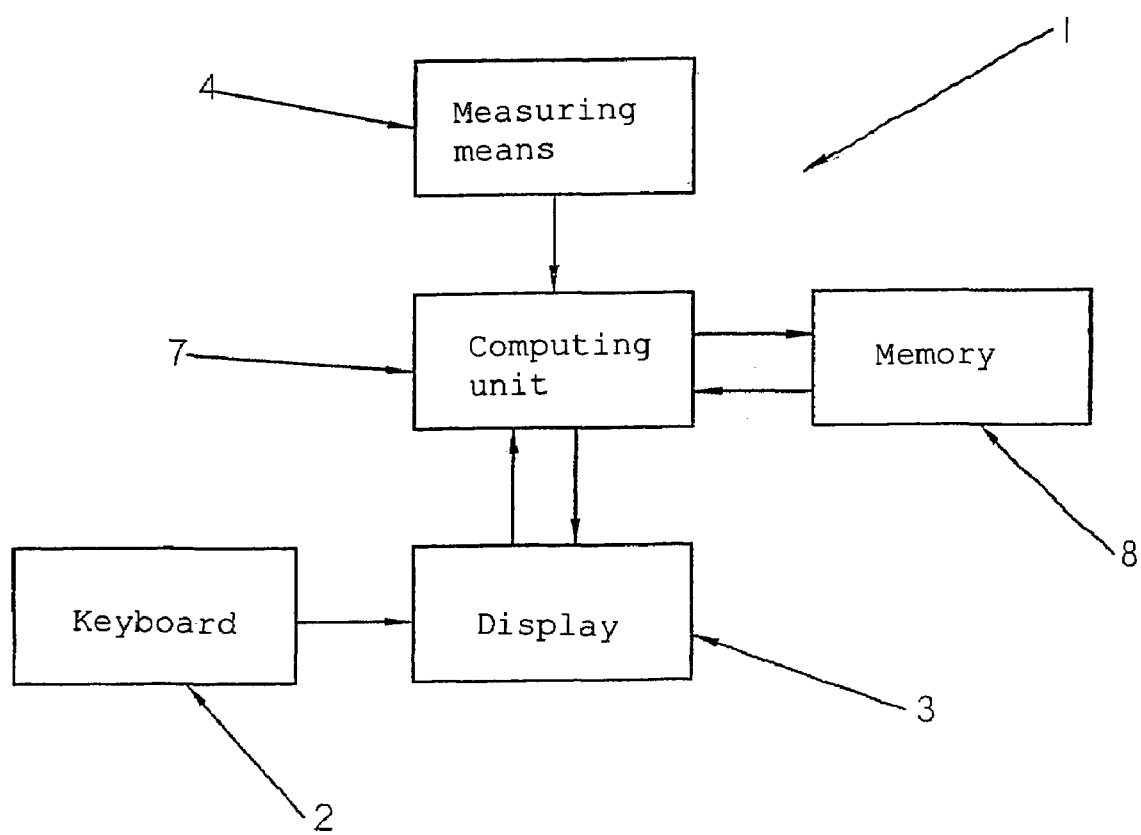
FIG. 2 is a block diagram of the main constituent parts of the apparatus.

In FIG. 2 is represented a block diagram of the operation of such an apparatus where measuring means 4 are constituted by weighing cells and the electrodes of the apparatus that transmit the measured signals to a computing unit 7, notably a microprocessor or microcontroller adapted to the treatment to be effectuated. Computing unit 7 is connected to a memory 8 adapted to store data specific to the individual, such as the data measured by measuring means 4 as well as identification data introduced by the user on keyboard 2. The values computed by computing unit 7 or stored in memory 8 are displayed by display 3. These values can be weight, quantity of fat mass, quantity of lean mass, the BMI (ratio between weight and square of the height), the water content of the organism, or any other parameter computed on the basis of the bioelectric impedance of the body of the individual.

Figure 3:
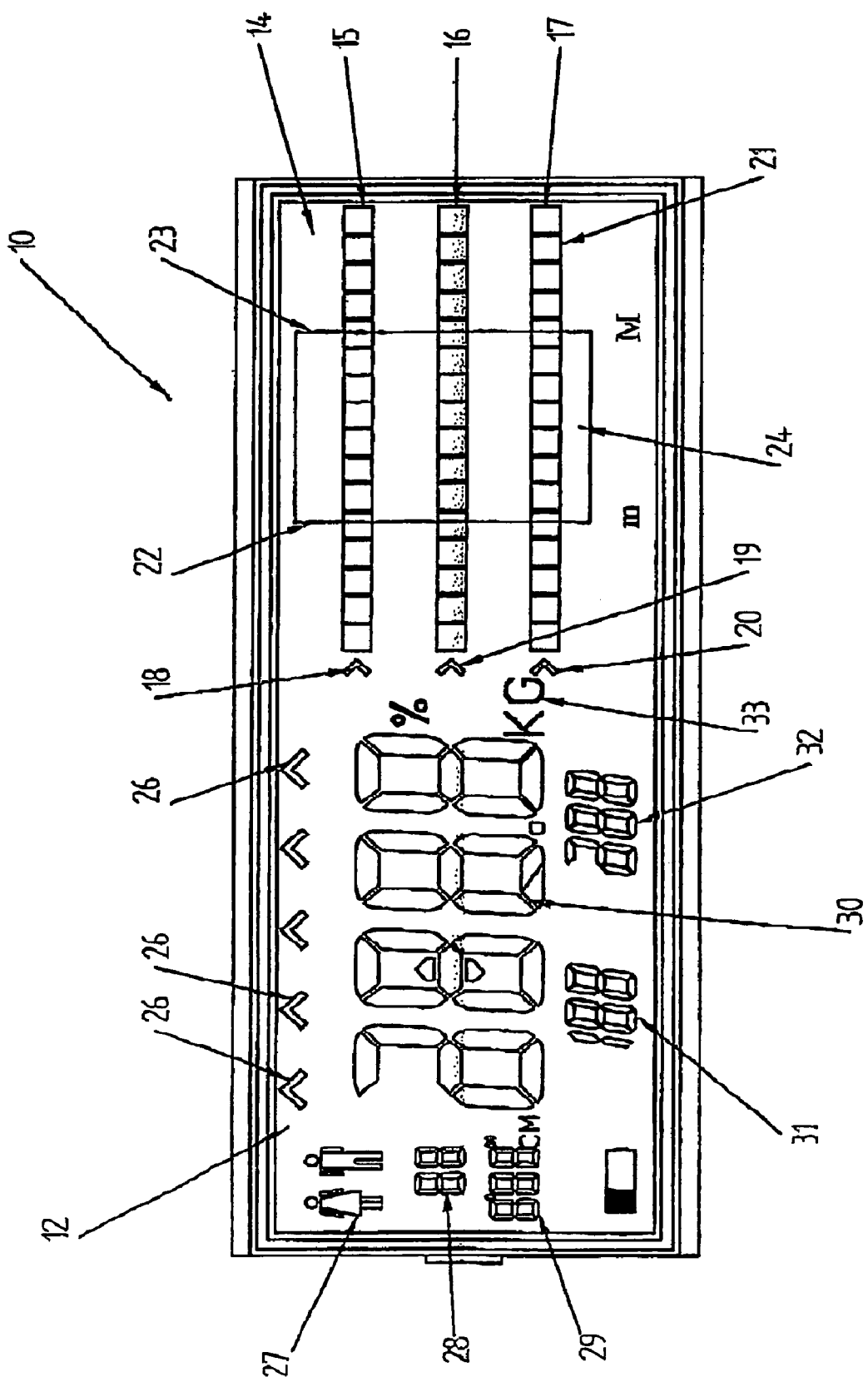
FIG. 3 represents a top view of a display according to a first embodiment of the invention.

Display 3 has a liquid crystal display screen 10 which is shown in FIG. 3. Display screen 10 of elongated form has a first digital display zone 12 and a second graphic display zone 14 disposed in an extension of the first.

As shown in FIG. 3, digital display zone 12 has several groups of numbers and symbols constituted on the basis of segments that show the values specific to the user, inputted via keyboard 2 or measured by apparatus 1. Thus, field 27 represents the gender of the user, field 28 indicates the age and field 29 the height in cm or in inches of the user. Field 30 indicates in large characters the current value of the parameter measured or computed by the apparatus, a value that is followed by the unit of measurement associated with the measured parameter, represented in the field 33. Fields 31 and 32 show the lower, respectively upper limits of normality of the measured parameter. These values are evaluated by computing unit 7 as a function of data specific to the user, notably the height, age, gender, previously inputted with the aid of a keyboard 2 and entered into memory 8 of apparatus 1. In digital display zone 12, arrows 26 permit the user of the apparatus to be identified, in this case, the five cursors indicate the storage and selection of the result of the data specific to five users.

Graphic display zone 14 is constituted by three parallel horizontal axes 15,16,17, each having a cursor 18,19,20 at one of its ends. Cursors 18,19,20 form the linkage with digital display zone 12 by informing the user on the measured parameter. In the example presented in FIGS. 3 and 4, on axis 15 is represented the weight of the user, on axis 16 the quantity of fat mass and on axis 17 the quantity of lean mass.

On each of the axes 15,16,17 is represented the current value of a measured parameter. This value is represented with respect to a normality zone 24 delimited by two vertical lines 22,23 that cross horizontal axes 15,16,17. Each representation axis 15,16,17 is provided in the form of a line constituted by a succession of segments or points, comprises between 10 and 20 points, preferably 16 points. Vertical lines 22,23 delimit on each axis a normality interval having a width comprised between 5 and 7 points, which permits a good framing of the measured value at the interior or to one side and the other of the normality interval for all users.

Vertical lines 22,23 are preferably marked permanently on the protective part of liquid crystal screen 10. This protective part is preferably at least partially transparent to permit reading of screen 10. Vertical lines 22,23 can be marked with ink or paint, silk screened or engraved in relief by any mechanical or chemical process on the upper part of screen 10. In order to better mark a normality zone 24, it is preferred to delimit, on the upper part of screen 10, a rectangle having as its sides the lines 22,23. One can equally inscribe in the lower part of each of lines 22,23 by the same process, the marks m and M corresponding to the lower, respectively upper, limit of the normality zone.

When the apparatus is first placed into operation, the user begins by programming his personal data. Thus, he inputs his data via keyboard 2, notably button 2b to select the values and buttons 2a,2c for moving in the decreasing, respectively increasing, direction on digital part 12 of screen 10. He thus inputs the height in field 29, age in field 28 and gender in field 27, and he then attributes a personalized touch to all of these data that will be stored and then read out at each new operation of the apparatus by the same person.

Figure 4:
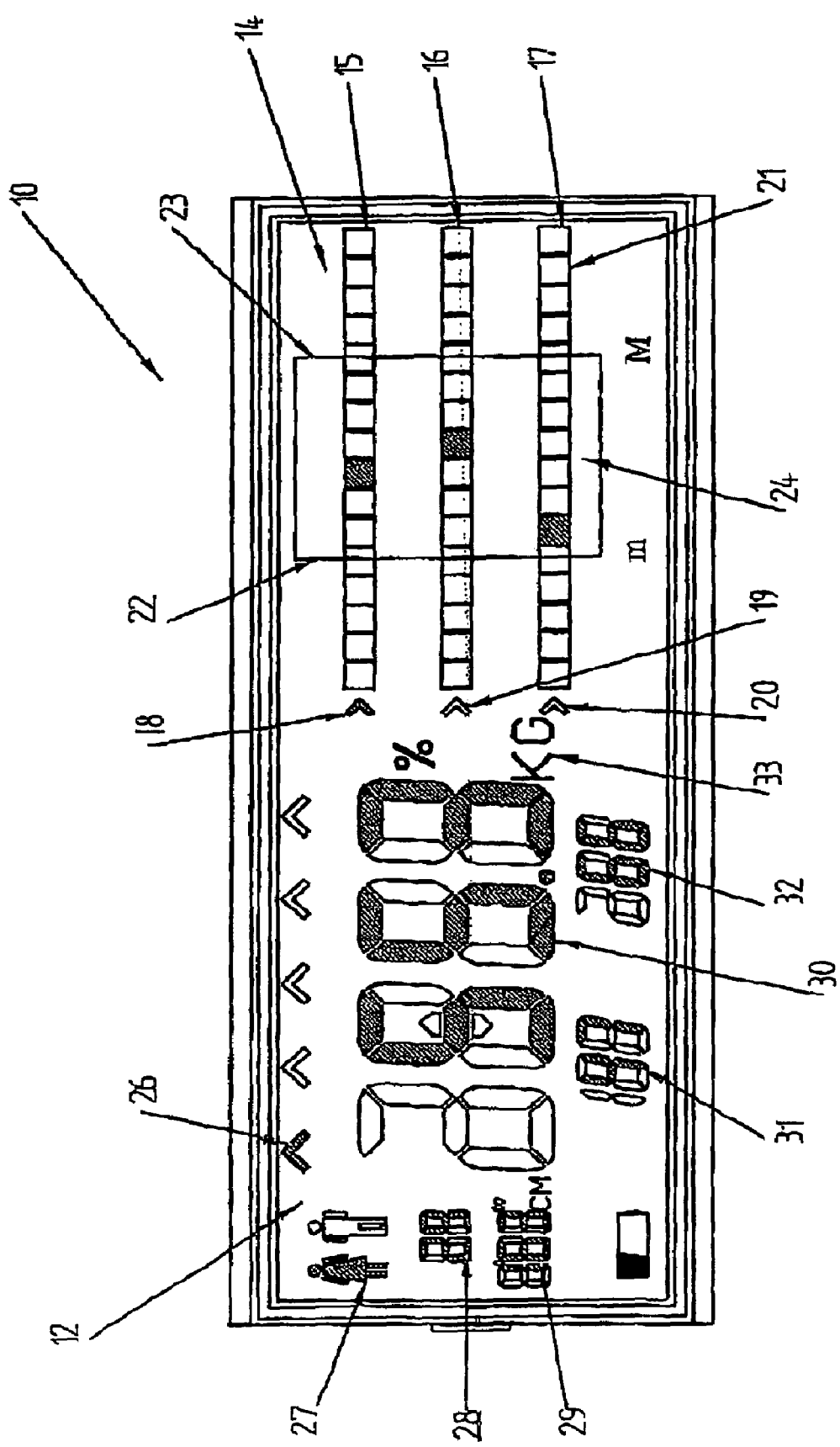
FIG. 4 is a top view of the display of FIG. 3 showing an example of the display of values measured or computed by the apparatus.

One example of use of the apparatus is presented in FIG. 4, where arrow 26 is illuminated and corresponds to the user identified by his data inscribed in fields 27,28 and 29. The user is recognized by the apparatus as soon as he mounts on the platform of the measuring scale. These personal data are displayed on the screen and several moments after the apparatus measures and computes the data of the body composition of the individual. These data are displayed in digital part 12 and in graphic part 14.

At each measurement interval, screen 10 of the display indicates the current measured value, starting by displaying the weight in field 30, such as is visible in FIG. 4. At the same time, there are displayed the normality limits of the weight of the user, notably the lower limit in field 31 and the upper limit in field 32. Then, computing unit 7 effectuates calibration of the scale of graphic representation of the weight on axis 15. For this, at each point 21 axis 15 attributes thereto a value calculated by dividing the value of the normality interval by the number of points corresponding to the interval. Once the scale is calibrated for the axis of representation of weight 15, the display positions the current measured value on axis 15 by illuminating the point corresponding to its position. Cursor 18 is equally illuminated to alert the user to the digital values inscribed in fields 30,31, 32, on their correspondence with limits m,M and the representation on axis 15. The user thus regards the digital values in zone 12 and compares them to their graphic representation in zone 14.

The same display process is applied to represent the values of the quantity of fat mass on axis 16, respectively of the lean mass on axis 17.

Digital display of the current values and of their upper and lower limits can advantageously be done in alternation, by a succession of the values of each parameter in a predetermined time interval. In order to alert the user on the parameter represented in graphic zone 14, the corresponding cursor 18, 19 or 20 is illuminated and blinks, as well as the representation point on representation 15,16 or 17 while the corresponding digital values are inscribed successively in the corresponding fields of digital zone 12. One can thus, for example, visualize the representation of the current weight of the user blinking on axis 15 during 10 s, then the point representing the quantity of fat mass blinking on axis 16 during a same time period, and finally the point of the quantity of lean mass that blinks during a same duration, while the other two remain illuminated, but fixed. Thus, the digital values and their graphic representations can be visualized and compared continuously for each of the three measured parameters.

Points 21 remain illuminated continuously on axes 15,16, 17, which permits a comparison to be effectuated of the three parameters one with respect to the other and with respect to the normality zone which has the same size for all of the parameters. This permits each user to establish his own diagnostic and to follow the evolution thereof, for example the shift of the values with respect to the limits of the normality zone. This also permits a determination if there is a disequilibrium or not between the three parameters compared. Thus, a vertical alignment in normality zone 24 of the three parameters: weight, fat mass and lean mass can reveal a well balanced body composition.

Figure 5:
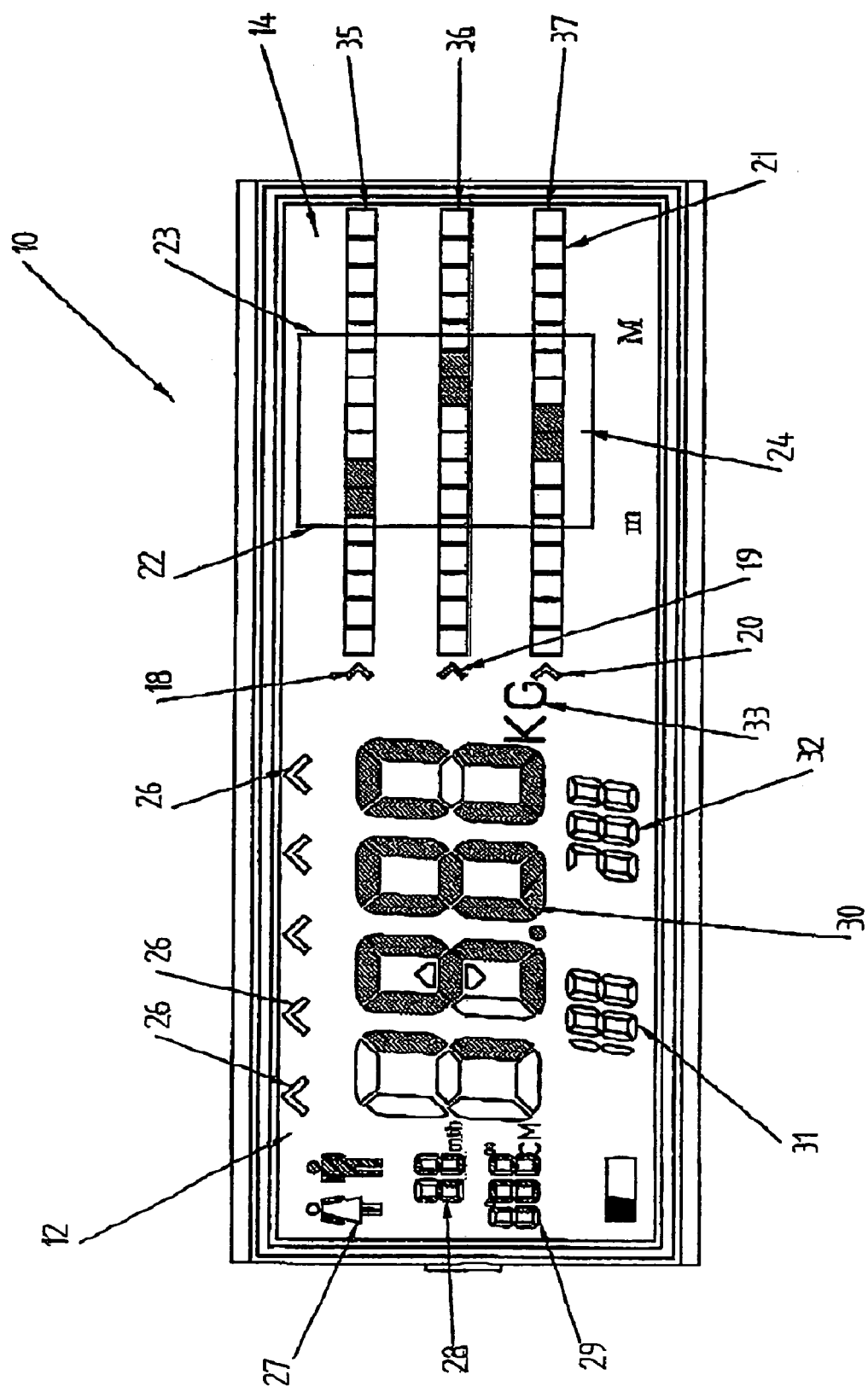
FIG. 5 is a top view of a display according to a second embodiment of the invention, showing an example of display of values measured or computed by the apparatus.

FIG. 5 illustrates a display according to a second embodiment of the invention, notably a display associated with a child scale or a baby scale. Measuring means 4 associated with such an apparatus generally comprise a weight receiving platform supported by weight sensors composed of strain gauges that transmit an electric signal representative of the weight measured to an electronic circuit having a computing unit 7, a memory 8 and a display 3 connected to a keyboard 2.

Such a weighing apparatus can integrate, in an advantageous manner, an electronic height gauge or a displacement sensor associated with a movable assembly being displaced with respect to a fixed mark of the apparatus, permitting automatic measurement of the height, or length, of the child who is present on the weight reception platform and then transmission to computing unit 7 or to memory 8. In a variant, the known height is inputted directly via keyboard 2 by the parent. Other characteristics of the child (gender, age) are equally inputted by means of keyboard 2 and stored.

As is visible in FIG. 5, liquid crystal display screen 10 has a digital display zone 12 and a graphic display zone 14. Digital display zone 12 permits display, on the one hand, of inputted values such as the nature of the gender of the child 27, age 28, and, on the other hand, values measured or computed by the apparatus, such as the weight, height or body mass index.

Field 30 indicates, in large characters, the current value of the parameter measured or computed by the apparatus, with its unit of measurement represented in zone 33. Fields 31 and 32 show the upper and lower statistical or normality values of the measured or computed parameter, evaluated by computing unit 7, taking into account the age, gender of the child, or even its height.

Graphic display zone 14 has three parallel horizontal axes 35,36,37, each axis end having, at the side of the adjacent digital display zone 12, a cursor 18, 19, 20 identifying the parameter whose value is displayed in field 30. In FIG. 5, on axis 35 is represented the value of the height or length measured by the apparatus or manually inputted on axis 36 that of the weight measured by the apparatus and on axis 37 that of the body mass index computed by the apparatus.

The current measured, inputted or computed values indicated on axes 35,36,37 are represented with respect to a zone of normality 24 delimited by a rectangle appearing on the display. Thus, as in the previously described embodiment, the scale of representation of each value measured, inputted at the keyboard or computed by the apparatus is adjusted in a fashion such that the zones of normality have the same width. Thus, left vertical line 22 of zone of normality 24 indicates the theoretical lower limit and right vertical line 23 of this zone of normality indicates the theoretical upper limit.

Thus, the display of FIG. 5 permits simultaneously displaying in a graphic manner, on parallel axes, the height, or length, of the child, his weight and computed body mass index and to relate these three parameters to a zone of normality, all while having the digital value inscribed in an adjacent digital display zone. This permits a better visualization of the results and observing how the child relates to the zone of normality.

A display of the type described in FIG. 5 is not limited to use in the framework of a baby scale or a child scale, but it can be applied equally to a bathroom scale, by adapting the structure of the apparatus and the computing means to display the height, the weight and the body mass index of an adult.

Other variants or embodiments of the invention can be imagined without departing from the framework of its claims. Thus, one can imagine the use of a display according the invention with an apparatus having a different structure adapted to measure a biological parameter such as: temperature, blood pressure, pulse, heart rhythm, etc. One can equally envision replacing the digital representation by a display of the analog type controlled, for example, by a stepping motor.

The invention claimed is:

1. Apparatus for measuring a biological parameter of an individual, said apparatus comprising: measuring means (4) for measuring the biological parameter; computing means (7) for computing a range of normality values of said parameter as a function of data specific to the individual; and a display (3) that is integrated into said apparatus and is connected to said computing means for graphic representation (14) of the measured parameter relative to a representation axis (15), characterized in that said computing means is operative to adjust the position of the graphic representation of said measured parameter on said display with respect to a reference zone on said display representing the computed normality range, the reference zone being delimited to one side and the other of said axis by a fixed mark (m, M) in combination with at least one adjacent digital indication (30,31,32).

2. Apparatus according to claim 1, characterized in that said computing means (7) effectuate a calibration of the graphic representation scale as a function of the value attributed to the width of the zone comprised between the two fixed marks (m,M).

3. Apparatus according to claim 1, characterized in that said fixed marks (m,M) delimit, to one side and the other of the center of said axis (15), an interval of normality (24) of the measured parameter.

4. Apparatus according to claim 1, characterized in that said display (3) is adapted to graphically represent at least two distinct parameters simultaneously.

5. Apparatus according to claim 4, characterized in that said display (3) is adapted to display digital indications of one parameter at a time, and that it comprises means for switching over to the display of digital indications of another parameter.

6. Apparatus according to claim 5, characterized in that said display (3) is adapted to display intermittently the digital indications of each parameter and that it has a cursor linking the graphic representation to the digital indication of said parameter.

7. Apparatus according to claim 4, characterized in that said at least two parameters are represented on parallel axes (15,16,17).

8. Apparatus according to claim 7, characterized in that said marks (m,M) are constituted by two parallel lines (22,23) that cross said axes (15,16,17) and define a zone of normality (24) for the measured parameters.

9. Apparatus according to claim 8, characterized in that said parallel lines (22,23) are vertical.

10. Apparatus according to claim 4, characterized in that said parameters are the weight, the quantity of fat mass, and the quantity of lean mass of the individual.

11. Apparatus according to claim 4, characterized in that said parameters are the height, the weight, and the body mass index.

12. Apparatus according to claim 1, characterized in that the graphic representation axis (15,16,17) of said display (3) is constituted by a succession of 10 to 20 points.

13. Apparatus according to claim 1, characterized in that it is adapted to represent the biological parameters specific to several individuals.

14. Apparatus according to claim 1, characterized in that it further comprises a memory and means for placing in said memory measured values and for display of the history of the evolution of the measured values over a predetermined period.

15. Apparatus for measuring the body composition of an individual, said apparatus comprising: measuring means (4) for measuring at least one parameter of the body composition of the individual; computing means (7) for computing a range of normality values of the at least one parameter of the body composition; and a display (3) that is integrated into said apparatus and is connected to said computing means for graphic representation (14) of the measured parameter with respect to a representation axis (15), characterized in that said computing means is operative to adjust the position of the graphic representation of said measured parameter on said display with respect to a reference zone on said display representing the computed normality range, the reference zone being delimited to one side and the other on said axis (15) by a fixed mark (m,M) in combination with at least one adjacent digital indication (30,31,32).

16. Bathroom scale or child's scale comprising: means (4) for measuring at least the weight of an individual; computing means (7) for computing range of normality values of the weight of the individual parameter as a function of data specific to the individual; and a display (3) that is integrated into said apparatus and is connected to said computing means for graphic representation (14) of the measured and/or computed values with respect to a representation axis (15), characterized in that said computing means is operative to adjust the position of the graphic representation of the measured and/or computed values on said display with respect to a reference zone on said display representing the computed normality range, the reference zone being delimited to one side and the other on said axis by a fixed mark (m, M) in combination with at least one adjacent digital indication (30,31,32).

17. Process for measuring at least one biological parameter of an individual, comprising: measuring the value of at least one parameter selected from the weight and height of the individual; storing in memory the at least one measured value; computing at least one further biological parameter selected from the quantity of fat mass, quantity of lean mass and body mass index of the individual, based on the measured value and computing a range of normality values of the at least one further biological parameter as a function of data specific to the individual; producing a graphic display of the at least one further biological parameter with respect to a representation axis in combination with at least one digital indication; and adjusting the position of the graphic representation of the at least one further biological parameter with respect to a reference zone delimited at one side and the other on said axis by fixed marks.

18. A process for displaying at least one biological parameter of an individual, comprising:

determining the value of at least one biological parameter of the individual, the at least one parameter being selected from among weight, quantity of fat mass, quantity of lean mass and body mass index; computing a range of normality values of the at least one parameter based on a function of data specific to the individual; displaying a graphic representation of the at least one parameter; and adjusting the position of the graphic representation of the at least one measured parameter on the display with respect to a reference zone on the display representing the computed normality range, the reference zone being delimited to one side and the other of said axis by fixed marks (m, M) in combination with at least one adjacent digital indication.

* * * * *